US010910110B1

(12) United States Patent
McNair

(10) Patent No.: US 10,910,110 B1
(45) Date of Patent: *Feb. 2, 2021

(54) FORECASTING ARTERIAL EMBOLIC AND BLEEDING EVENTS

(71) Applicant: CERNER INNOVATION, INC., Kansas City, KS (US)

(72) Inventor: Douglas S. McNair, Leawood, KS (US)

(*) Notice: Subject to any disclaimer, the term of this patent is extended or adjusted under 35 U.S.C. 154(b) by 1148 days.

This patent is subject to a terminal disclaimer.

(21) Appl. No.: 15/292,938

(22) Filed: Oct. 13, 2016

Related U.S. Application Data

(63) Continuation-in-part of application No. 14/837,324, filed on Aug. 27, 2015.

(60) Provisional application No. 62/241,122, filed on Oct. 13, 2015, provisional application No. 62/042,490, filed on Aug. 27, 2014.

(51) Int. Cl.
*G16H 50/50* (2018.01)
*A61B 5/02* (2006.01)
*A61B 5/00* (2006.01)
*G16H 10/60* (2018.01)

(52) U.S. Cl.
CPC ......... *G16H 50/50* (2018.01); *A61B 5/02042* (2013.01); *A61B 5/725* (2013.01); *A61B 5/7267* (2013.01); *A61B 5/746* (2013.01); *G16H 10/60* (2018.01)

(58) Field of Classification Search
CPC ...... G16H 50/50; G16H 10/60; A61B 5/7267; A61B 5/746; A61B 5/725; A61B 5/02042
See application file for complete search history.

(56) References Cited

U.S. PATENT DOCUMENTS 6,527,715 B2    3/2003   Balkin et al.
6,530,884 B2 *  3/2003   Balkin ................. A61B 5/4806
                                                      600/300

(Continued)

OTHER PUBLICATIONS

Lim, Ryoung K. Minh Q Phan; Richard W. Longman. State-Space System Identification with Identified Hankel Matrix. Department of Mechanical and Aerospace Engineering Technical Report No. 3045, Sep. 1998. Princeton University, Princeton, NJ (Lim). (Year: 1998) (Year: 1998).*

(Continued)

*Primary Examiner* — Linh Giang Le
(74) *Attorney, Agent, or Firm* — Shook, Hardy & Bacon, LLP

(57) ABSTRACT

Systems, methods and computer-readable media are provided for monitoring patients and quantitatively predicting whether an event such as a significant change in health status meriting intervention, is likely to occur within a future time interval subsequent to computing the prediction. Medical data for a patient is collected from one or more different inputs and used to determine time series data. From this, a forecasted numerical value is computed for one or more physiologic parameters associated with the patient, which may be used to further monitor the patient and facilitate decision making about a need for intensified monitoring or intervention to prevent or manage deterioration of hemostasis. An evolutionary algorithm, such as particle swarm optimization and/or differential evolution, may be used to determine the most probable value of the physiologic parameter(s) at one or more future times.

20 Claims, 10 Drawing Sheets

(56) References Cited

U.S. PATENT DOCUMENTS

| | | | |
|---|---|---|---|
| 6,561,992 B1* | 5/2003 | Eberhart | A61B 5/1101 600/595 |
| 7,880,607 B2 | 2/2011 | Olson et al. | |
| 8,041,417 B2 | 10/2011 | Jonckheere et al. | |
| 8,595,159 B2 | 11/2013 | McNair | |
| 9,532,721 B2* | 1/2017 | Batchinsky | A61B 5/7275 |
| 2012/0095300 A1 | 4/2012 | McNair | |
| 2012/0108916 A1 | 5/2012 | Riftine | |
| 2014/0081092 A1 | 3/2014 | McNair | |
| 2014/0118356 A1* | 5/2014 | van Ooijen | G06F 19/3456 345/440 |

OTHER PUBLICATIONS

S. N. Qasem and S. M. Shamsuddin, "Radial basis function network based on time variant multi-objective particle swarm optimization for medical diseases diagnosis," Applied Soft Computing Journal, vol. 11, No. 1, pp. 1427-1438, 2011.*

Roy Chowdhury, S., Chakrabarti, D., and Saha, H., Medical diagnosis using adaptive perceptive particle swarm optimization and its hardware realization using FPGA. Journal of Medical Systems, in press, 2008.*

Notice of Allowance received for U.S. Appl. No. 14/837,324, dated Jun. 26, 2019, 11 pages.

Chowdhury et al., "Medical Diagnosis Using Adaptive Perceptive Particle Swarm Optimization and its Hardware Realization Using FPGA", Journal of Medical Systems, in press, 2008, 20 pages.

Qasem et al., "Radial Basis Function Network Based on Time Variant Multi-Objective Particle Swarm Optimization for Medical Diseases Diagnosis", Applied Soft Computing Journal, 2011, vol. 11, pp. 1427-1438.

First Action Interview Pre-Interview Communication dated May 4, 2018 in U.S. Appl. No. 14/837,324, 5 pages.

Final Office Action received for U.S. Appl. No. 14/837,324, dated Feb. 12, 2019, 15 pages.

Lim et al., "State-Space System Identification with Identified Hankel Matrix", Department of Mechanical and Aerospace Engineering Technical Report No. 3045, Sep. 1998, 36 Pages.

Price, Kenneth V., et al.; Differential Evolution, A Practical Approach to Global Optimization; Springer-Verlag Berlin Heidelberg, 2005; pp. 1-539. (Hard Cover Book mailed on Feb. 28, 2017 in U.S. Appl. No. 15/291,792).

Final Office Action received for U.S. Appl. No. 14/087,411, dated Apr. 1, 2015, 7 pages.

First Action Interview Office Action received for U.S. Appl. No. 14/087,411, dated Jan. 12, 2015, 7 pages.

First Action Interview Office Action received for U.S. Appl. No. 14/837,324, dated Aug. 9, 2018, 6 pages.

Notice of Allowance received for U.S. Appl. No. 13/270,748, dated Jul. 19, 2013, 12 pages.

Notice of Allowance received for U.S. Appl. No. 14/087,411, dated Apr. 22, 2015, 7 pages.

Preinterview First Office Action received for U.S. Appl. No. 14/087,411, dated Oct. 3, 2014, 5 pages.

Cao et al., "Predicting ICU Hemodynamic Instability Using Continuous Multiparameter Trends", Engineering in Medicine and Biology Society, 30th Annual International Conference of the IEEE, Aug. 20-24, 2008, pp. 3803-3806.

Fitzmaurice et al., "Regression Models for a Bivariate Discrete and Continuous Outcome with Clustering", Journal of the American Statistical Association, vol. 90, No. 431, Sep. 1995, pp. 845-852.

Gagne, Nathalie, "Developing a Non-Invasive Method to Monitor Cardiovascular Control during Orthostatic Challenge Considering the Limitation of the Finometer", Thesis, University of Waterloo Masters, Waterloo, available at <http://uwspace.uwaterloo.ca/handle/10012/4299>, Mar. 25, 2009, 109 pages.

Kojadinovic et al., "Modeling Multivariate Distributions with Continuous Margins Using the Copula R Package", Journal of Statistical Software, vol. 34, No. 9, May 2010, pp. 1-20.

Kumar et al., "Copula Based Prediction Models: An Application to an Aortic Regurgitation Study", BMC Medical Research Methodology, vol. 7, No. 21, 2007, 9 pages.

Liu et al., "Ellipsoidally Symmetric Extensions of the General Location Model for Mixed Categorical and Continuous Data", Biometrika, vol. 85, No. 3, 1998, pp. 673-688.

Olkin et al., "Multivariate Correlation Models with Mixed Discrete and Continuous Variables", The Annals of Mathematical Statistics, 1961, pp. 448-465.

Regan et al., "Likelihood Models for Clustered Binary and Continuous Outcomes: Application to Developmental Toxicology", Biometrics, vol. 55, Sep. 1999, pp. 760-768.

Silva et al., "Mortality Assessment in Intensive Care Units via Adverse Events Using Artificial Neural Networks", Artificial Intelligence in Medicine, vol. 36, 2006, pp. 223-234.

Stell et al., "A Clinical Grid Infrastructure Supporting Adverse Hypotensive Event Prediction", in Proceedings of the 9th IEEE/ACM International Symposium on Cluster Computing and the Grid (CCGRID'09), 2009, pp. 508-513.

Zeger et al., "Feedback Models for Discrete and Continuous Time Series", Statistical Sinica, vol. 1, 1991, pp. 51-64.

* cited by examiner

| ITEM | VALUE |
|---|---|
| SENSITIVITY | 85% |
| SPECIFICITY | 99% |
| EVENT PREVALENCE | 26% |
| POSITIVE PREDICTIVE VALUE (PPV) | 98% |
| NEGATIVE PREDICTIVE VALUE (PPV) | 95% |
| FALSE POSITIVE RATE | 0.0% |
| FALSE NEGATIVE RATE | 5.1% |

```
###########################################################################

#  PLOT ROC

##################################################################### library(pROC)

ds4 <- read.csv(file="c:/0_cerdsm/0__math_models/INR_coag/roc.csv")
roc1 <- roc(ds4[,1] ~ ds4[,2], percent=TRUE,
# arguments for auc
# partial.auc=c(100, 90), partial.auc.correct=TRUE,
#  partial.auc.focus="sens",
# arguments for ci
  ci=TRUE, boot.n=100, ci.alpha=0.9, stratified=FALSE,
# arguments for plot
#  auc.polygon=TRUE, max.auc.polygon=TRUE,
  plot=TRUE, grid=TRUE, print.auc=TRUE, show.thres=TRUE)
sens.ci <- ci.se(roc1, specificities=seq(0, 100, 5))
plot(sens.ci, type="shape", col="lightblue")
plot(sens.ci, type="bars")

roc(ds4[,1] ~ ds4[,2], ds4, plot=TRUE)
```

*FIG. 3C*

```
###########################################################################

# Particle Swarm Optimization prediction of arterial thromboembolic events/
# hypercoagulability from short INR time series in chronic/recurrent atrial fibrillation
# patients on warfarin

##################################################################### library(pso)

initialization
# passing NA in e or y[4,4] throws error
# e <- runif(6)  # may not converge
e <- rep(0.01,6)
thresh <- 1.85
pctile <- 0.025 psooptim control, vectorized but still only uses 1 core
ctrl <- list(reltol=2e-01, abstol=5e-01, maxf=1e04, maxit=1e03, maxit.stagnate=1e02,
        vectorize=TRUE, c.p=1.8, c.g=1.8, w=c(0.7,0.9), s=50, p=0.8,
        hybrid=TRUE, hybrid.control=list(maxit=1e03), trace=0, REPORT=1000)
# dsm$par    contains vector of epsilon adjustments
dsm$value contains minimized value of hankel.obj when fnscale=1 alternate control
ctrl <- list(reltol=2e-01, abstol=5e-01, maxf=1e04, maxit=1e03, maxit.stagnate=1e02,
        vectorize=TRUE, c.p=1.2, c.g=1.2, w=c(0.5,0.5), s=30, p=0.5,
        hybrid=TRUE, hybrid.control=list(maxit=1e03), trace=0, REPORT=1000)

# EWMA smoothing
lambda <- 0.7
# inline slightly faster than recursion
ewma6 <- function(s) {
    p1 <- lambda*s[1,2] + (1 - lambda)*s[1,1]
    p2 <- lambda*s[1,3] + (1 - lambda)*p1
    p3 <- lambda*s[1,4] + (1 - lambda)*p2
    p4 <- lambda*s[2,4] + (1 - lambda)*p3
    r <- lambda*s[3,4] + (1 - lambda)*p4
    return(r)
  }
```

. . .

CONTINUES IN FIG. 4B

*FIG. 4A*

CONTINUES FROM FIG. 4A

.
.

```
# hankel objective function
hankel.obj.pso <- function(e) {
    e1 <- e[1]
    e2 <- e[2]
    e3 <- e[3]
    e4 <- e[4]
    e5 <- e[5]
    e6 <- e[6]
    x11 <- y[1,1]
    x12 <- y[1,2]
    x13 <- y[1,3]
    x14 <- y[1,4]
    x21 <- y[2,1]
    x22 <- y[2,2]
    x23 <- y[2,3]
    x24 <- y[2,4]
    x31 <- y[3,1]
    x32 <- y[3,2]
    x33 <- y[3,3]
    x34 <- y[3,4]
    x41 <- y[4,1]
    x42 <- y[4,2]
    x43 <- y[4,3]
    x44 <- y[4,4]
    z <- ewma6(y)
    a <- x11 + e1
    b <- x12 + e2
    c <- x13 + e3
    d <- x14 + e4
    e <- x24 + e5
    f <- x34 + e6
    x44 <- ((a*c*e - a*d^2 + b*c*d - e*b^2 + b*c*d - c^3)^-1)*(-d*(b*d*f - b*e^2 + c*d*e - f*c^2 + c*d*e - d^3)
                                        +e*(a*d*f - a*e^2 + e*c^2 - b*c*f + b*d*e - c*d^2)
                                        -f*(a*c*f - a*d*e + b*c*e - f*b^2 + b*d^2 - d*c^2))
    y[4,4] <<- x44
    # implement det(x) inline, allowing for mixed double-float and integer numeric storage.mode
    detx <- x11*x22*x33*x44 + x11*x32*x43*x24 + x11*x42*x23*x34
        + x21*x12*x43*x34 + x21*x32*x13*x44 + x21*x42*x33*x14
        + x31*x12*x23*x44 + x31*x22*x43*x14 + x31*x42*x13*x24
        + x41*x12*x33*x24 + x41*x22*x13*x34 + x41*x32*x23*x14
        - x11*x22*x43*x34 - x11*x32*x23*x44 - x11*x42*x33*x24
        - x21*x12*x33*x44 - x21*x32*x43*x14 - x21*x42*x13*x34
        - x31*x12*x43*x24 - x31*x22*x13*x44 - x31*x42*x23*x14
        - x41*x12*x23*x34 - x41*x22*x33*x14 - x41*x32*x13*x24
    abs(detx*(0.1666667*sum(abs(e1),abs(e2),abs(e3),abs(e4),abs(e5),abs(e6)) + abs(x44 - z))^-1)
}
```

CONTINUES IN FIG. 4C

CONTINUES FROM FIG. 4B

.
.

```
# hankel matrix examples to solve with y[4,4] non-NULL dummy value, preferably EWMA
estimate
# may need to add small amount of noise to y to avoid det(x) = 0
# if solver converges, the forecast is value of y[4,4]
# lower and upper parms can be extrema of plausible values
# even if solver does not converge in maxit or maxf, the $par array does contain plausible
estimates for y[3,3]
iterate N times and take the range as plausible prediction interval for next value y5 function to transform time series 4-vector to matrix for Hankel difference equation model
vec6.trans <- function(v){
  if (length(v) != 6) stop("wrong time series length")
  tmp <- matrix(rep(0,16), ncol=4)
  tmp[1,1:4] <- v[1:4]
  tmp[2,1:4] <- v[2:5]
  tmp[3,1:4] <- v[3:6]
  tmp[4,1:3] <- v[4:6]
  y <<- tmp
} function to calculate 5th percentile of next INR result from 1000 trials of Particle Swarm
Optimization forecasting of difference equation from 4 previous INR values
psonext.ae <- function(v){
  y5 <- rep(NA, 1000)
  y <- vec6.trans(v)
  y[4,4] <- ewma6(y)
  ul <- mean(y) + 4*sd(y)
  ll <- mean(y) - 4*sd(y)
  for (i in 1:1000) {
    set.seed(as.numeric(Sys.time()))
    dsm <- psoptim(e, hankel.obj.pso, lower=ll, upper=ul, control=ctrl)
    if(dsm$convergence > 0 || y[4,4] < 0)
    {
      y5[i] <- median(dsm$par)
    }else{
      y5[i] <- y[4,4]
    }
  }
  quantile(y5,pctile) < thresh
}

#-----------------------------
# true-positive <1.4>
inr <- c(2.3,2.5,1.9,2.3,1.8,1.7)
psonext.ae(inr)

# true-positive <1.4>
inr <- c(2.4,2.3,2.2,2.1,1.8,1.7)
psonext.ae(inr)

# true-positive <1.4>
inr <- c(4.9,5.1,4.2,2.5,1.8,1.7)
psonext.ae(inr)
.
.
```

*FIG. 4C*

CONTINUES IN FIG. 4D

CONTINUES FROM FIG. 4C

.
.

```
# true-positive <1.5>
inr <- c(1.8,2.0,2.0,1.9,1.8,1.8)
psonext.ae(inr)

#----------------------------
# true-negative <1.9>
inr <- c(3.3,3.6,4.3,6.0,6.0,4.9)
psonext.ae(inr)

# true-negative <1.9>
inr <- c(3.1,4.2,4.5,4.1,2.9,2.4)
psonext.ae(inr)

# true-negative <1.9>
inr <- c(2.7,2.9,3.0,2.4,1.9,1.8)
psonext.ae(inr)

# true-negative <2.0>
inr <- c(1.8,1.9,2.1,2.0,1.9,2.1)
psonext.ae(inr)

# true-negative <2.3>
inr <- c(2.1,2.0,2.6,2.4,2.5,2.1)
psonext.ae(inr)

# true-negative <2.4>
inr <- c(1.9,2.1,2.5,2.6,2.5,2.6)
psonext.ae(inr)

# true-negative <2.4>
inr <- c(2.2,2.2,2.5,2.6,2.6,2.5)
psonext.ae(inr)

# true-negative <2.7>
inr <- c(2.0,2.2,2.4,3.0,3.1,3.0)
psonext.ae(inr)

#----------------------------
# false-positive <x.x>

<none>

#----------------------------
# false-negative <1.1>
inr <- c(1.8,1.7,2.7,1.9,1.9,2.1)
psonext.ae(inr)

# false-negative <1.7>
inr <- c(2.0,2.1,2.7,2.7,2.5,2.5)
psonext.ae(inr)

# false-negative <1.7>
inr <- c(3.2,2.4,8.2,3.8,5.8,2.9)
psonext.ae(inr)

# false-negative <1.7>
inr <- c(2.4,3.3,3.9,5.4,5.6,3.0)
psonext.ae(inr)
```

*FIG. 4D*

| case (502) | seq (504) | age_cat (506) | gender (508) | inr (510) |
|---|---|---|---|---|
| 3 | 0 | 2 | F | 2.9 |
| 3 | 1 | 2 | F | 2.7 |
| 3 | 2 | 2 | F | 1.9 |
| 3 | 3 | 2 | F | 1.9 |
| 3 | 4 | 2 | F | 2.1 |
| 3 | 5 | 2 | F | 1.1 |
| 5 | 0 | 3 | F | 2.4 |
| 5 | 1 | 3 | F | 3 |
| 5 | 2 | 3 | F | 3.1 |
| 5 | 3 | 3 | F | 3 |
| 5 | 5 | 3 | F | 2.7 |
| 8 | 0 | 3 | M | 1.9 |
| 8 | 1 | 3 | M | 2.1 |
| 8 | 2 | 3 | M | 2.2 |
| 8 | 3 | 3 | M | 1.8 |
| 8 | 4 | 3 | M | 1.6 |
| 8 | 5 | 3 | M | 1.7 |
| 8 | 6 | 3 | M | 1.5 |
| 8 | 7 | 3 | M | 1.4 |
| 8 | 8 | 3 | M | 2 |
| 8 | 9 | 3 | M | 1.7 |
| 8 | 10 | 3 | M | 2.3 |
| 8 | 11 | 3 | M | 2.4 |
| 8 | 12 | 3 | M | 2.7 |
| 8 | 13 | 3 | M | 2.7 |
| 8 | 14 | 3 | M | 2.7 |
| 8 | 15 | 3 | M | 2.5 |
| 8 | 19 | 3 | M | 2.5 |
| 8 | 20 | 3 | M | 1.6 |
| ... | | | | |
| 237 | 0 | 1 | M | 3.6 |
| 237 | 1 | 1 | M | 1.5 |
| 237 | 2 | 1 | M | 3.5 |
| 237 | 4 | 1 | M | 2.4 |
| 237 | 7 | 1 | M | 1.2 |
| 237 | 8 | 1 | M | 1.3 |
| 239 | 0 | 0 | M | 5.7 |
| 239 | 1 | 0 | M | 4.5 |
| 239 | 2 | 0 | M | 2.9 |
| 239 | 3 | 0 | M | 1.9 |
| 239 | 4 | 0 | M | 1.9 |
| 239 | 5 | 0 | M | 2.2 |
| 239 | 6 | 0 | M | 2.1 |

FIG. 5.

FORECASTING ARTERIAL EMBOLIC AND BLEEDING EVENTS

CROSS-REFERENCE TO RELATED APPLICATIONS

This application claims the benefit of U.S. Provisional Application No. 62/241,122, titled "Forecasting Arterial Embolic and Bleeding Events," filed Oct. 13, 2015; this application is a continuation-in-part and claims benefit of U.S. Nonprovisional patent application Ser. No. 14/837,324, filed Aug. 27, 2015, titled "Forecasting Clinical Events From Short Physiologic Timeseries," which claims the benefit of U.S. Provisional Application No. 62/042,490, filed Aug. 27, 2014, titled "Forecasting Clinical Events From Short Physiologic Timeseries," each of which is expressly incorporated by reference in its entirety.

BACKGROUND

Major problems in delivery of safe and effective care services in hospitals involve deficiencies in the quality and continuity of patient care, including the monitoring of each patient's condition over time. Despite recent advances in electronic health records (EHR) systems, the present state of the art in medical care within hospitals still does not in general utilize the accruing medical record information for active, prognostic use-cases, to predict the future status or events or outcomes that are likely to materialize for the patient. Instead, in many scenarios the EHR acts mainly as a passive repository for documenting and storing the information that is generated by each provider and each department, which characterizes the current or previous status or outcomes that have already materialized.

During ongoing patient management in situations requiring anticoagulation, such as atrial fibrillation or transient ischemic attack or stroke, each patient may over a period of time see many doctors and many nurses. Such fragmentation of responsibility for the care process challenges the ability of each provider to quickly and accurately grasp the meaning of the constellation of accumulating clinical and laboratory facts about the patient, to understand trends that may be developing in the patient's health status, and to evaluate the urgency of attention that is necessary to effectively address existing or newly developing issues or to successfully prevent potential adverse events and complications. Even more, many doctors and nurses are unable to forecast a patient's future homeostasis or coagulation status with certainty or particularity. While there have been attempts to provide a technological solution, technology has largely failed to provide a reliable and accurate solution.

The consequence of relatively infrequent assessment of coagulation status, often in coagulation clinics at intervals of 2 weeks or more, when combined with the all-too-common fragmentation of the care process with responsibilities divided among dozens of provider personnel most of whom do not have deep or longstanding familiarity with the patient, is that unexpected deterioration of hemostasis occurs to many patients, such that a medical crisis ensues. In many such instances, the impending deterioration could have been predicted—provided that more frequent (international normalized ratio) INR monitoring were acquired in advance; provided that that data were integrated into a suitably accurate personalized predictive model; and provided that the output of the model were effectively communicated to the providers who have the responsibility to intervene and prevent or manage the predicted risk of deterioration.

SUMMARY

Systems, methods and computer-readable media are provided for monitoring patients and quantitatively predicting whether or not a significant change in their blood coagulation status meriting intervention is likely to occur within the next inter-observation monitoring time interval subsequent to computing the prediction. In particular, embodiments of the disclosure provide for monitoring the clinical and physiologic status of a patient in a hospital, such as by generating near-term forecasts, which may be presented to caregivers, that indicate a patient's risk trend during his/her coagulation management. In some embodiments, the forecasts may be periodically plotted and/or displayed to a caregiver of the patient.

Recognizing a high risk of deterioration far enough in advance of the onset of deterioration can guide rational allocation of resources, including intensified monitoring or treatments that may achieve reduction of risks of arterial thromboembolic events and/or hemorrhagic events in the context of atrial fibrillation or other health conditions, decreased length-of-stay in acute care institutions, financial savings, or other benefits.

Some embodiments can accommodate rapid-drift non-differentiable processes. For example, by using algebraic evolution solvers staggered in time. These solvers may operate in parallel, and each successively converges and returns its result to another solver that combines a plurality of the serialized results into a combined ensemble forecast for the value that will be measured at the next observation. Accordingly, these embodiments do not require that the serial measurements be made at precise, periodic intervals but instead tolerate significant clock or phase jitter in the measured time series. In an embodiment, an interface module is provided for receiving incoming medical data from a patient, a transformation module for transforming the medical datum into forecasted value, and a combination module for combining successive forecasts into single value.

In this way, some embodiments enable physicians, nurses and clinical researchers to provide more safe and effective care for each patient, especially those who have admissions lasting several days or more. In addition or alternatively, some embodiments assist hospitals in preventing and reducing the frequency of crises in hemostasis by using the systems' capability to recognize trends in a patient's plasma clotting factor system responsiveness before the patient deteriorates or reaches a crisis. As such, current embodiments provide for a counter-conventional technological solution that is unknown in the industry and the area of clinical support.

Accordingly, in one aspect, one or more patients are periodically monitored to collect serial medical or clinical data about the patient(s) from one or more different inputs, which may be used to determine time series data. Based on the time series data, a forecast or prediction is computed periodically for one or more physiologic parameters and used to further monitor the patient and facilitate decision making about a need for intensified monitoring or intervention to prevent or manage physiologic or hemodynamic deterioration. For example, numerical heart rate and systolic blood pressure data may be acquired and used for calculating a shock index, or similar composite variable, which may be stored as a plurality of serial determinations over time, thereby forming a timeseries. The time series then may be used to forecast a numerical value of the index at one or a plurality of future time points. An evolutionary algorithm, such as particle swarm optimization or differential evolution, may be used to solve for the most probable value of the physiologic variable or composite variable at a plurality of future time points.

In another aspect, date-time stamped medical data about a patient is received from one or more data sources. The medical data may comprise data points from a plurality of times. Using data from a plurality of time points, such as 6 or more in one embodiment, a predicted physiologic parameter at a future particular time for the patient may be calculated. From this, data analysis and classification may be performed to determine or predict the state of the patient's systemic physiology.

According to some embodiments, the hospital patient's clinical and/or physiological status may be tracked continually during their admission or for a portion of that time. In this way, embodiments of the disclosure may facilitate physicians, nurses and clinical researchers providing safer and more effective care for each patient, especially those who have admissions lasting several days or more. In addition or alternatively, some embodiments may assist hospitals in preventing and reducing the frequency of medical crises by using a system or method embodiment's capability to recognize trends in a patient's autonomic nervous system responsiveness before the patient deteriorates or reaches a crisis. Recognizing a high risk of deterioration far enough in advance of the onset of deterioration can guide rational allocation of resources, including intensified monitoring or treatments that may achieve reduction of risks of arterial thromboembolic events and/or hemorrhagic events in the context of atrial fibrillation or other health conditions, decreased length-of-stay in acute care institutions, financial savings, or other benefits.

BRIEF DESCRIPTION OF THE DRAWINGS

The present disclosure is described in detail below with reference to the attached drawing figures, wherein:

FIGS. 3A-3C depict receiver operating characteristic (ROC) curve and statistical performance of an embodiment of the disclosure as applied to the computation of forecasts for the shock index, in accordance with an example embodiment actually reduced to practice, and a corresponding computer program routine for plotting the ROC curve;

FIGS. 4A-4D depict an embodiment of a computer program routine for determining a probable future value of a physiologic variable or composite variable using PSO, in accordance with the example embodiment actually reduced to practice; and FIG. 5 depicts documented hemostasis data of target patients utilized in the example embodiment described in connection to FIGS. 4A-4D.

DETAILED DESCRIPTION

Figure 1A:
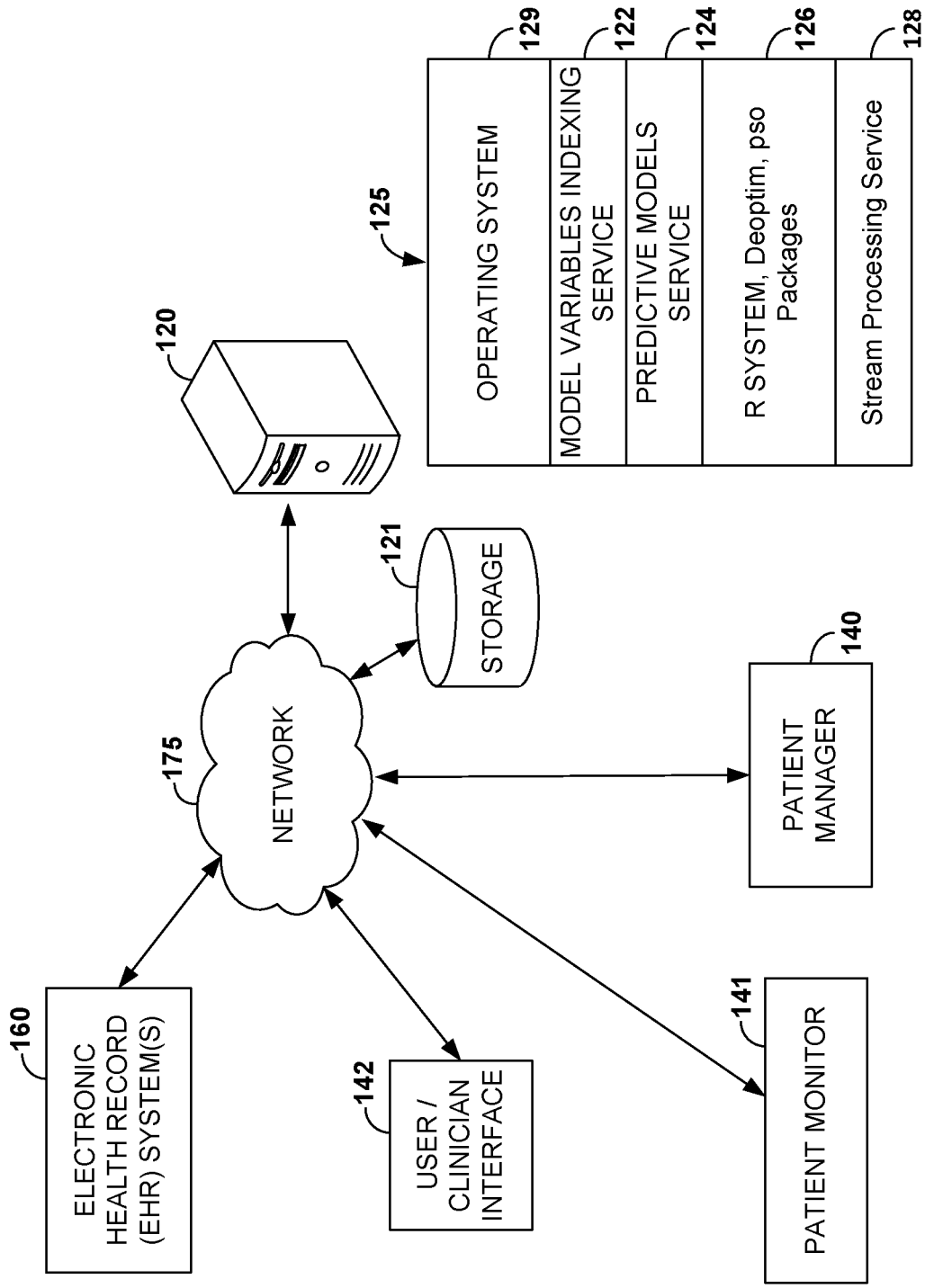
FIGS. 1A and 1B depict aspects of an illustrative operating environment suitable for practicing an embodiment of the disclosure.

The subject matter of the present disclosure is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the disclosure may be embodied as, among other things: a method, system, or set of instructions embodied on one or more computer readable media. Accordingly, the embodiments may take the form of a hardware embodiment, a software embodiment, or an embodiment combining software and hardware. In one embodiment, the embodiment takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Accordingly, embodiments of the disclosure are provided for monitoring patients and quantitatively predicting whether or not an event such as a significant change in their health status meriting intervention, is likely to occur within a next or future inter-observation monitoring time interval subsequent to computing the prediction. For example, some embodiments determine and provide a numerical probability of such an event in patients by near-term forecasts generated for a patient, which may be periodically plotted or displayed to show the particular patient's risk trend during his or her hospital stay. Some embodiments include an interface module for receiving incoming medical data from a patient, a transformation module or service for transforming the medical datum into forecasted value, and a combination module or service for combining successive forecasts into single value.

As described above, one of the consequences of relatively infrequent assessment of coagulation status, often in coagulation clinics at intervals of 2 weeks or more, when combined with the all-too-common fragmentation of the care process with responsibilities divided among dozens of provider personnel most of whom do not have deep or long-standing familiarity with the patient, is that unexpected deterioration of hemostasis occurs to many patients, such that a medical crisis ensues. In many such instances, the impending deterioration could have been predicted—provided that more frequent INR monitoring were acquired in advance; provided that that data were integrated into a suitably accurate personalized predictive model; and provided that the output of the model were effectively communicated to the providers who have the responsibility to intervene and prevent or manage the predicted risk of deterioration.

Potentially life-threatening deterioration of patients' coagulation status may arise while under treatment with warfarin or other anticoagulants. Excessive blood-thinning effect may be associated with severe bleeding and, conversely, inadequate (sub-therapeutic) blood-thinning effect may be associated with arterial thromboembolic phenomena such as stroke, myocardial infarction, or embolization of kidneys or other organs and tissues. In many instances, the INR time series of individual patients may be labile due to genetic or genomic variations that affect the pharmacokinetics of anticoagulant medications.

In some cases, temporally evolving changes in liver metabolism or passive congestion of the venous circulation may cause INR time series to be volatile with wide day-to-day changes. In yet other cases, day-to-day variations in patient diet and Vitamin K intake and/or patient adherence to the medication regimen result in unexpected volatility of hemostasis measurements. In still other cases, time-varying consumption of plasma clotting factors arises due to intermittent atrial fibrillation and resultant stasis in the left atrium and elsewhere in the vasculature.

Frequently, however, there is no obvious or apparent abnormality in the prothrombin time (PT) or International Normalized Ratio (INR) or other clinical or laboratory variables that precedes the deterioration and, in such instances, ordinary threshold transgressions of the nominal limits of the therapeutic range are inadequate, frequently giving a 'false-negative' assurance that there will be no near-term deterioration in the patient's status when in fact deterioration does materialize.

In other instances, fluctuations in the values of INR or other variables that are utilized give rise to 'false-positive' alarms, incorrectly identifying a given patient as one in whom acute bleeding or clotting is likely when in fact no such event occurs. In such a situation, valuable resources associated with intensified monitoring or other interventions are misapplied. The resources are allocated to the given patient, in whom those resources are not in fact necessary and provide no benefit, and, insofar as resources are finite and in short supply, those resources are during that same time interval withheld from other patients, for whom the resources might have provided greater value and benefit.

Thus, a significant limitation of conventional approaches is that they suffer from limited statistical sensitivity and specificity, with substantial false-negative and false-positive rates. Most of the prior art regression equations or CART or decision-tree or neural-network or other classification algorithms are able only to achieve receiver operating characteristic (ROC) area-under-the-curve (AUC) discrimination performance lower than 75%. Thus, they fail to achieve the accuracy and efficiency of the embodiments described herein. This means that the practical applications of the embodiments described herein lead to a significant impact in clinical support systems and the health-care industry in general.

Another limitation of conventional approaches is that the variables that are included in the predictions are often temporally 'lagging indicators' (such as serum albumin or other metabolic indicators of liver function), which broadly characterize a background of diminished organ-system capacity related to synthesis and metabolism of blood plasma clotting factors.

Yet another limitation of conventional approaches is that the predictive models typically rely upon measurements that are often performed in an imprecise and inconsistent manner. For example, measurement of bleeding time ought in principle to be a relatively accurate and precise process. However, haste and poor technique on the part of the observer often cause bleeding time measurements to be in error by many tens of seconds. It is practically impossible to compel improvements by busy caregivers who are prone to make imprecise and inconsistent measurements. As a result, any point-estimate or single-point-in-time predictor that is based on variables whose values tend to be subject to inaccuracy, imprecision and inconsistency in measurement technique tend to generate wide variations in predicted risk. By contrast, variables whose measurements do not present such difficulties (such as INR, either by traditional laboratory testing means or by home INR monitor devices that can be used by the patient or their in-home caregiver) are amenable to more accurate, precise predictions.

Some embodiments of the disclosure provide systems and methods for calculating and communicating a numerical probability of an event in patients, and especially patients in whom other scores yield excessive false-negative results. Despite the superior sensitivity to accurately recognize patients at-risk whose abnormalities are not obvious, embodiments simultaneously achieve specificity that is superior to the prior art. The ROC AUC of the present embodiments of the disclosure is greater than 90% in the populations examined to-date. In part, this greater accuracy and discriminatory power to classify individual cases correctly is due to the embodiment's utilization of evolutionary timeseries analytical methods, especially particle-swarm optimization (PSO) and differential evolution (DE) algorithms, which enable inferences based on a short time-series consisting of a small plurality of observational timepoints (data from as few as 6 serial measurement epochs). In some embodiments, evolutionary analysis estimates the statistical forecast for the next epoch immediately beyond the present one.

There are some deterioration events that are acute, with sudden onset and no apparent antecedent abnormality or multivariate cluster of abnormalities that predict the imminent event. Fortunately from the screening and diagnostic perspective, a majority of patients who deteriorate have a prodrome of coagulation abnormalities for many hours in advance of the onset of deterioration. This affords a 'window of opportunity' sufficient for undertaking effective preventive and corrective actions and intensified monitoring so as to intervene more quickly and effectively than would otherwise tend to occur.

In many instances, the prodrome involves a change in statistical relationships (autocorrelation of one variable with itself; cross-correlations between pairs of variables) that bear on the natural physiologic coupling between the organ systems and processes that give rise to the measured variables; for example, the relation INR to central venous pressure, embodied in composite functions of these variables, such as INR*CVP in the context of acute care.

The statistical distributions of the values taken on by the terms in such derived, composite variables are both skewed and asymmetric, both under normal conditions and under various pathophysiologic conditions that give rise to actionable events that relate to medical outcomes.

The practical reality, however, is that statistical tests of the goodness-of-fit of distributions to data require a considerable number of observations in order to produce a reliable conclusion or p-value. In the present embodiment, the model development dataset and model validation dataset were able to generate stable, reliable p-values for PSO or DE forecasts based on as few as 6 prior measurements, either of the INR by itself or of derived variables such as INR*CVP.

The failure to recognize incipient and emerging clinical deterioration in patients in general hospital wards leads to delays in patient management. Such worsening physiology is associated with an increase in hospital mortality in the critically ill and adult hospital inpatients. Such a state is often characterized by significant disturbances in hemostasis parameters for 12 h to 24 h or more. The failures and delays lead to adverse events including unexpected admissions to the intensive care unit (ICU) and unexpected deaths [McGloin1999]. Earlier intervention, prevention of deterioration, and improvement in patient outcome require a series of steps including vital sign documentation and interpretation; subsequent meaningful communication and timely and appropriate medical management.

However, even basic and essential measurements, such as INR, are ordinarily documented infrequently. Reasons for the failures to recognize emerging clinical deterioration include nonoptimal observation and charting processes and incomplete understanding of how and why vital signs are meant to be measured and acted upon. There frequently is also a failure to communicate the patient's changing status to appropriate responsible care providers, a failure which delays appropriate medical management.

Early warning scores have recently been developed to improve detection and communication by categorizing the patient's severity of illness and prompting nursing staff to initiate a medical review or other intervention at specific decision and action levels. However, such early warning scores suffer from significant limitations as set forth above. The present embodiment avoids most of the limitations of the prior art and achieves superior predictive accuracy and statistical discrimination compared to other scores. It does so (a) by analyzing physiologic time series as arising from an 'algebraic evolution' and (b) processing the resulting array of information so as to generate a predicted value for the time series at one or more future time points.

Subtle patterns in coagulation measurements may presage departures from the therapeutic range for INR, which in turn can lead to hemorrhagic events or clotting and thromboembolic events. Early detection of such coagulation patterns may lead to more timely treatment, less bleeding or clotting risk and reduced risk of death. But early detection cannot occur unless INR or other variables are measured sufficiently frequently. Frequent measurement is a strategy that has often been neglected but is now progressively improving since the introduction of small, inexpensive point-of-care prothrombin time (PT) or International Normalized Ratio (INR) testing devices. The time series comprised of serial measurements of INR may evolve relatively rapidly on a time-scale of 24 hours depending on the nature and severity of the emerging derangements. Accordingly, an embodiment of the disclosure seeks to solve Hankel matrix equations representing short time series of such values as an algebraic evolution and thereby produce accurate forecasts of near-term future values. A suitable solver for such equations may involve an objective function including minimizing the determinant of the Hankel matrix, in some embodiments.

Probability distributions whose moments (expected value, variance, etc.) are time-invariant are known as stationary distributions. If the distribution of objective function fluctuations is stationary and its expectation value is finite, then the optimal vector and the objective function can be reliably and accurately estimated. But the probability distributions of INR coagulation signals is, in general, non-stationary and is particularly so in the context of acute health care where the patient is experiencing some organ system state that is sufficiently abnormal to warrant their presenting to the health system seeking care or seeking guidance from the physician who is managing their anticoagulation regimen.

When an objective function's minimum is non-stationary, its moving average location drifts and the optimization goal is one of tracking the optimal vector on short sequences of observations or short time-scales or both. In the case of acute-care monitoring where the status of the patient often changes relatively quickly, the optimum may drift rapidly. Further, the systems that give rise to the measured data tend to embody a chaotic, stochastic process for which least-mean-square or recursive least-square deterministic optimizer that requires estimating a derivative with respect to time does not produce forecasts of adequate accuracy.

Accordingly, some embodiments of the disclosure entail a system or method that can accommodate rapid-drift non-differentiable processes. In particular, such embodiments initialize algebraic evolution solvers staggered in time. These solvers operate in parallel, and each successively converges and returns its result to another solver that combines a plurality of the serialized results into a combined ensemble forecast for the value that will be measured at the next observation. Thus such embodiments do not require that the serial measurements be made at precise, periodic intervals but instead tolerates significant clock or phase jitter in the measured time series.

Additionally, the embodiments of the disclosure overcome certain drawbacks associated with the prior art by providing a means for longitudinally calculating and tracking the patient's risk of acute deterioration while in a hospital. Further, some embodiments provide a predicted probability of acute deterioration for a hospitalized patient.

In an embodiment, there is provided a system or method for generating an indicator of a patient's probability of acute deterioration, the system including a data module receiving data relating to a patient's vital signs, a data transformation and statistical computation module generating an output from the data, the output representing the patient's likelihood of deteriorating acutely, and a display module displaying the output.

As described above, in some embodiments, an evolutionary algorithm, such as particle swarm optimization or differential evolution, may be used to solve for the most probable value of the physiologic variable or composite variable at a plurality of future time points. Particle swarm optimization (PSO) is an algorithm that performs population-based stochastic search and optimization. It originated from computer simulation of individual 'particles', such as members of a flock of migratory birds flying or a school of fish swimming. Swarms comprising many individuals establish an overall direction of movement collectively and socially, in a self-organizing manner that responds to optimum directions initially undertaken by one or a few individual members. Each particle keeps track of its own position in the search space and its own best solution so far achieved. The PSO process also keeps track of the globally best solution achieved by the swarm.

During the exploration across the search space with discrete-time iterations, the velocity of each PSO agent is computed as a function of the best position of the swarm, the best personal position of each particle, and its previous velocity. These components contribute randomly to the position of each particle in the next iteration or generation of the swarm. Together, the generations exhibit a tendency toward survival of the fittest and global best in terms of minimizing the objective function. The probability of success is increased due to the large number of particles in the swarm, since success requires merely that one member of the swarm succeed. As such, PSO is able to efficiently discover correct global optima even when presented with optimization search spaces that have many local minima and nonlinearities or discontinuities.

Differential evolution (DE) is an evolutionary algorithm that has similarities to so-called genetic algorithms (GA). But DE has certain differences insofar as it is applicable to real-valued vectors rather than bit-encoded strings. Accordingly, the DE algorithm's mutation and cross-over operations are different from those in GA. Notably, the mutation operator is different in its way of becoming trapped in local minima of the function being optimized Like PSO, DE has population members or agents that effectively sample the search space of possible function values. For each successive generation of agents, mutation and cross-over operators can be applied to each agent's vector, a numerical objective function fitness is calculated, and the best of that generation's members are propagated to the next generation and the process is repeated until the fitness converges to an asymptotic value. If any agent achieves the objective fitness score or the maximum number of generations set as a limit, then the process is terminated.

Although inspired by nature, PSO and DE, and other such evolutionary algorithms are man-invented processes including multiple steps applying various mathematical operations or transforms in specific sequences and iterations. PSO and DE may be utilized for determining solutions to problems expressing phenomena in nonlinear wave motion, solution physics, Kortweg-de Vries equations, Kadomtsev-Petviashvili equations, and the nonlinear Schrödinger equation.

As described above, some embodiments of the disclosure include leveraging DE, PSO and/or other evolutionary algorithms in a process for determining a forecasted physiological event. Each evolutionary algorithm appears to possess strengths and limitations when used for particular applications in hemostasis variables forecasting, and various embodiments may use one, two, or more evolutionary algorithms. (For example, the results of two or more evolutionary algorithms may be combined using an ensemble model.) But regardless which of these algorithms maybe employed to solve the optimization under various embodiments of the disclosure, some embodiments further include novel processes utilizing Hankel matrices (which may be used as an algebraic evolution formalism) of similar objective functions of the type disclosed herein.

Referring now to the drawings in general, and initially to FIG. 1A in particular, an aspect of an operating environment 100 is provided suitable for practicing an embodiment of our disclosure. We show certain items in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure embodiments of the disclosure. Thus for readability, we show and reference items in the singular (while fully contemplating, where applicable, the plural).

As shown in FIG. 1, example operating environment 100 provides an aspect of a computerized system for compiling and/or running embodiments of monitoring patients and quantitatively predicting whether or not an event, such as a significant change in their health status meriting intervention, is likely to occur within a next or future inter-observation monitoring time interval subsequent to computing the prediction. Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or a plurality of EHR systems such as hospital EHR systems, health information exchange EHR systems, ambulatory clinic EHR systems, psychiatry/neurology EHR systems, and may be implemented in computer system 120. Similarly, EHR system 160 may perform functions for two or more of the EHR systems (not shown).

Network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system 160 include one or more data stores of health records, which may be stored on storage 121, and may further include one or more computers or servers that facilitate the storing and retrieval of the health records. In some embodiments, EHR system 160 may be implemented as a cloud-based platform or may be distributed across multiple physical locations. EHR system 160 may further include record systems, which store real-time or near real-time patient (or user) information, such as wearable, bedside, or in-home patient monitors, for example.

Although FIG. 1A depicts an exemplary EHR system 160, it is contemplated that an embodiment relies on user manager 140 and/or monitor 141 for storing and retrieving patient record information such as information acquired from monitor 141.

Example operating environment 100 further includes provider user/clinician interface 142 communicatively coupled through network 175 to an EHR system 160. Although environment 100 depicts an indirect communicative coupling between interface 142 and EHR system 160 through network 175, it is contemplated that an embodiment of interface 142 is communicatively coupled to EHR system 160 directly. An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. A provider clinician application facilitates accessing and receiving information from a user or health care provider about a specific patient or set of patients for which the likelihood(s) of future events such as acute risk of deterioration are determined according to the embodiments presented herein. Embodiments of interface 142 also facilitates accessing and receiving information from a user or health care provider about a specific patient or population of patients including patient history; health care resource data; variables measurements, time series, and predictions (including plotting or displaying the determined outcome and/or issuing an alert) described herein; or other health-related information, and facilitates the display of results, recommendations, or orders, for example. In an embodiment, interface 142 also facilitates receiving orders for the patient from the clinician/user, based on the results of monitoring and predictions. Interface 142 may also be used for providing diagnostic services or evaluation of the performance of various embodiments.

An embodiment of patient manager 140 takes the form of a user interface and application, which may be embodied as a software application operating on one or more mobile computing devices, tablets, smartphones, front-end terminals in communication with back-end computing systems, laptops, or other computing devices. In an embodiment, manager 140 includes a Web-based application or set of applications usable to manage user services provided by an embodiment of the disclosure. For example, in an embodiment, manager 140 facilitates processing, interpreting, accessing, storing, retrieving, and communicating information acquired from monitor 141. In an embodiment, manager 140 sends an alarm indication directly to user/clinician interface 142 through network 175. In an embodiment, manager 140 sends a maintenance indication to provider clinician interface 142. In one embodiment of manager 140, an interface component may be used to facilitate access by a user (including a clinician/caregiver or patient) to functions or information on monitor 141, such as operational settings or parameters, user identification, user data stored on monitor 141, and diagnostic services or firmware updates for monitor 141, for example.

As shown in example environment 100, in one embodiment, manager 140 is communicatively coupled to monitor 141 and to network 175. In an embodiment, patient monitor 141 communicates via network 175 to computer 120 and/or provider clinician interface 142.

An embodiment of monitor 141 (sometimes referred to herein as hemostasis measurement device) comprises one or more sensor components operable to acquire clinical or physiological information about a patient, such as various types of physiological measurements, physiological variables, or similar clinical information associated with a particular physiological status of a patient, and which may be acquired periodically or as one or more time series. In an embodiment, monitor 141 comprises a hemostasis measurement device, such as an INR determining component. Monitor 141 may be embodied as a hospital.

In an embodiment, one or more sensor components of monitor 141 may comprise a bedside monitor or a user-wearable sensor component or sensor component integrated into the patient's environment, such as the home or hospital. Examples of sensor components of monitor 141 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about patient, such as the monitored variables, used according to the embodiment of the disclosure disclosed herein may be received from human measurements or automatically determined by sensors in proximity to the patient. For example, in one embodiment, a nurse periodically measures a patients' blood pressure and enters the measurement via manager 140 or interface 142.

Examples of physiological variables monitored by monitor 141 can include, by way of example and not limitation, heart rate, blood pressure, oxygen saturation (SoO2), central venous pressure, other vital signs or any type of measureable or determinable physiological or clinical variable associated with a patient, which may be used for forecasting a future value (of the measured variable, a composite variable based on one or more measured variables, or other factor determined at least in part from one or more measured variables) of a patient in order to facilitate clinical decision making.

In an embodiment, a monitor such as 141 comprises a sensor probe or instrument and a communication link that periodically transmits identification information and probe data to patient manager 140, so that the time series of monitored values is stored on patient manager 140, enabling the patient manager to form a raw binary alarm indication and/or a physiological variable decision statistic. In an embodiment, patient monitor 140 collects raw sensor information and performs signal processing, such as movement detection, kinematic modeling, distance and shape processing, velocity measurement, forming a physiological variable decision statistic, cumulative summing, trending, wavelet processing, thresholding, computational processing of decision statistics, logical processing of decision statistics, preprocessing or signal condition, etc., part or all of which may be performed on monitor 141, manager 140, interface 142, and/or computer system 120.

An embodiment of monitor 141 stores user-derived data locally or communicates data over network 175 to be stored remotely. In an embodiment, manager 140 is wirelessly communicatively coupled to monitor 141. Manager 140 may also be embodied as a software application or app operating on a user's mobile device. In an embodiment, manager 140 and monitor 141 are functional components of the same device, such as a device comprising a sensor and a user interface. In an embodiment, manager 140 is embodied as a base station, which may also include functionality for charging monitor 141 or downloading information from monitor 141.

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on monitor 141 or manager 140 for performing signal conditioning of the measured patient variable(s). In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and incldues operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interfaces 140 and 142. In some embodiments, interface 142 operates in conjunction with software stack 125.

In embodiments, variables indexing (or mapping) service 122 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke one or more computation services 126. In one embodiment software stack 125 includes predictive models service 124, which comprises the services or routines for forecasting future values of physiological variable(s), such as the example computer program routines illustratively provided in FIGS. 4A-4D.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including for example, DEoptim (for performing differential evolution) and pso (for performing particle swarm optimization) packages, or similar services. In an embodiment, computation services 126 include the services or routines, which may be embodied as one or more software agents or routines such as the example embodiments of computer program routines illustratively provided in FIGS. 4A-4D. Some embodiments of services 126 comprise a transformation component or service for transforming the physiological or clinical patient information into forecasted value, and a combination component or service for combining successive forecasts into single value. Embodiments of computation services 126 may use one or more services stream processing service(s) 128.

Stream processing service(s) 128 may be embodied using IBM InfoSphere stream processing platform, Twitter Storm stream processing, or similar complex event processing (CEP) platforms, frameworks, or services, which may include the user of multiple such stream processing services (in parallel, serially, or operating independently). In some embodiments service(s) 128 include the Apache Hadoop and Hbase framework, or similar frameworks operable for providing a distributed file system, and which in some embodiments facilitate or provide access to cloud-based services such as those provided by Cerner HealtheIntent®. In one embodiment, stream processing services 128 listens to at least one "channel" of patient information, which may be provided by patient monitor 141, as patient data or processed information becomes available. Some embodiments of the disclosure also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
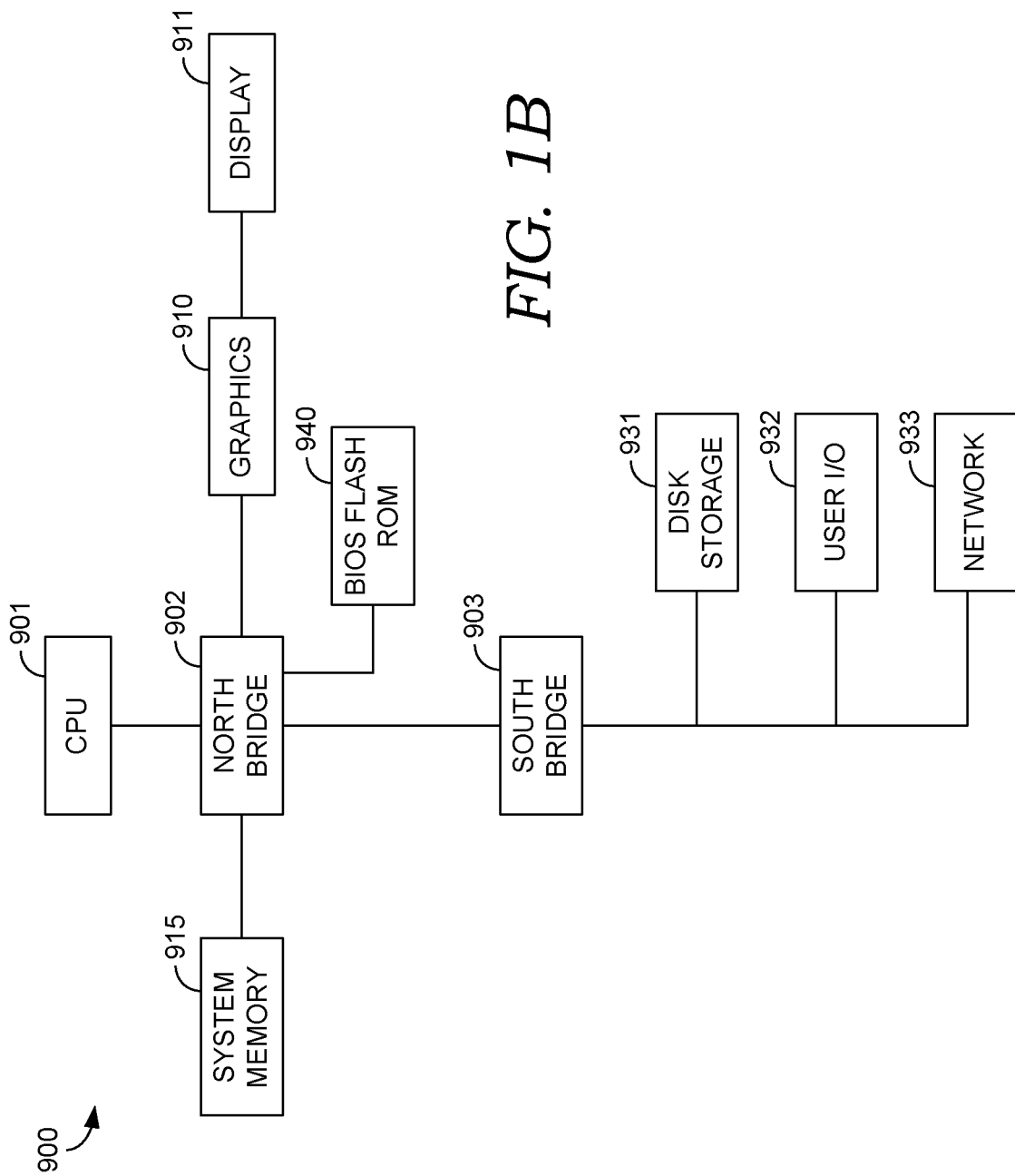

Turning briefly to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
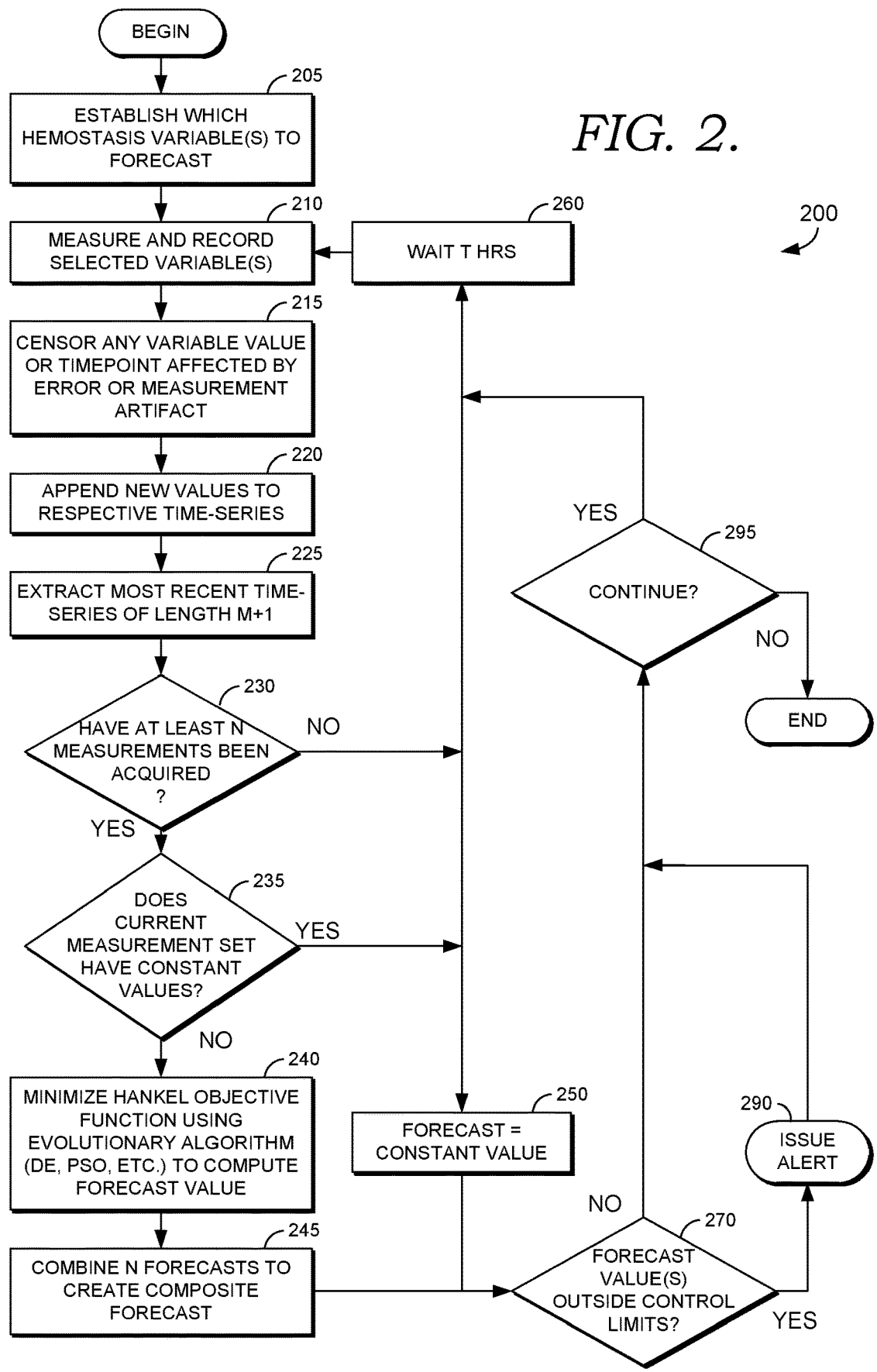
FIG. 2 depicts a flow diagram of a method for facilitating clinical decision making by determining a probability for a future clinical condition of a hospitalized patient, in accordance with an embodiment of the disclosure.

Turning now to FIG. 2, a method 200 is provided for determining a patient's risk of acute deterioration, and in particular predicting the likelihood that an event, such as a significant change in their health status meriting intervention, is likely to occur within a next or future inter-observation monitoring time interval, in some embodiments. With reference to method 200, at a high level some embodiments of the disclosure perform time series forecasting, which has traditionally presented a challenge in many fields of science and engineering. Generally, the object of time series forecasting is to build a model of the process and then use this model on the last values of the time series to extrapolate past behavior into future. Forecasting procedures include different techniques and models. Moving averages techniques, random walks and trend models, exponential smoothing, state space modeling, multi-variate methods, vector autoregressive models, cointegrated and causal models, methods based on neural, fuzzy networks or data mining and rule-based techniques are typical methods used in time series forecasting. But some embodiments of the disclosure provide a new method for the identification of an optimal set of time lags based on non-uniform attractor embedding from the observed non-linear time series. For example, a simple, deterministic method for the determination of non-uniform time lags comprises the pre-processing stage of the time series forecasting algorithm.

In particular, a near-optimal set of time lags may be identified by evolutionary algorithms, such as Particle Swarm Optimization (PSO) or Differential Evolution (DE). The solution fitness objective function may be constructed in such a way that it represents the spreading of the attractor in the delay coordinate space but does not contain any information on prediction error metrics. A weighted one-point crossover rule enables an effective identification of near-optimal sets of non-uniform time lags which are better than the globally optimal set of uniform time lags, in one embodiment. Thus, the reconstructed information on the properties of the underlying dynamical system is directly elaborated in these prediction systems and methods.

Accordingly, in forecasting physiologic variables, one embodiment of the disclosure identifies 'skeleton algebraic sequences' associated with short-term time series of the variables. The concept of the rank of the Hankel matrix is exploited to detect a base algebraic fragment of the time series. Particle swarm optimization and evolutionary algorithms are then used to remove the noise and identify the skeleton algebraic sequence that characterizes the time series and the underlying dynamical physiologic system that gives rise to the series.

A Hankel matrix H(m) is constructed from the elements of the time series sequence $x = \{x_0, x_1, x_2, \ldots, x_k\}$:

$$H^{(m)} = \begin{bmatrix} x_0 & x_1 & \ldots & x_{m-1} \\ x_1 & x_2 & \ldots & x_m \\ \vdots & & \ddots & \vdots \\ x_{m-1} & x_m & \ldots & x_{2m-2} \end{bmatrix} \quad (1)$$

Determinants of Hankel matrices are denoted by det $H^{(m)}$. The rank of the sequence x is an integer m that satisfies the following conditions:

$$\det H^{(m+k)} = 0 \text{ and } \det H^{(m)} \neq 0, \text{ for all } k. \quad (2)$$

If x is a completely chaotic, random sequence then m=∞ (the sequence does not have a defined finite rank). However, if the sequence is not random and arises from an algebraic evolutionary process, then the following equality holds:

$$x_n = \sum_{k=1}^{r} \sum_{l=0}^{n_k-1} \mu_{kl} \binom{n}{l} \rho_k^{n-1}, \quad (3)$$

where the characteristic roots ρk, k=1, 2, . . . , 4 can be determined from the Hankel characteristic equation:

$$\det \begin{bmatrix} x_0 & x_1 & \ldots & x_m \\ x_{m-1} & x_m & \ldots & x_{2m-1} \\ \vdots & & \ddots & \vdots \\ 1 & \rho & \ldots & \rho^m \end{bmatrix} = 0 \quad (4)$$

where the coefficients $\mu_{kl}$ can be determined from a system of linear algebraic equations (3) for different values of n.

Due to natural imprecision of measurement and various sources of noise in physiologic signals, the assumption that a sequence of such measurements is an algebraic evolution is, at best, an approximation. Forecasting the next element x2n from (1) and (2) is not in general possible due to the inherent superimposed noise in real-world time series. Therefore, some embodiments of the present disclosure propose a set of adjustment or noise-compensating error terms, such that the next (seventh) element to be forecast in a 6-element timeseries represented by a 4×4 Hankel matrix is:

$$x[4,4] = ((ace - ad^2 + bcd - eb^2 + bcd - c^3)^{-1} * (-d(bdf - be^2 + cde - fc^2 + cde - d^3) + e(adf - ae^2 + ec^2 - bcf + bde - cd^2) - f(acf - ade + bce - fb^2 + bd^2 - dc^2)) \quad (5)$$

where $a = x[1,1] + \varepsilon_1$ $b = x[1,2] + \varepsilon_2$ $c = x[1,3] + \varepsilon_3$ $d = x[1,4] + \varepsilon_4$ $e = x[2,4] + \varepsilon_5$ $f = x[3,4] + \varepsilon_6$ Some embodiments of disclosure set forth an optimization fitness objective function to minimize, which is illustrated for the case of a sequence that is 6 elements in length:

$$F(x, \vec{e}) = \text{abs}\left[\det(x) * \left(\frac{1}{6} * \sum_{1}^{6} \text{abs}(e_i) + \text{abs}(x[4,4] - EWMA(x))\right)\right]^{-1} \quad (6)$$

where EWMA is an exponentially-weighted moving average of the subset of the already-acquired elements in the sequence upon which the forecast is to be based.

Figures 3A, 3B:
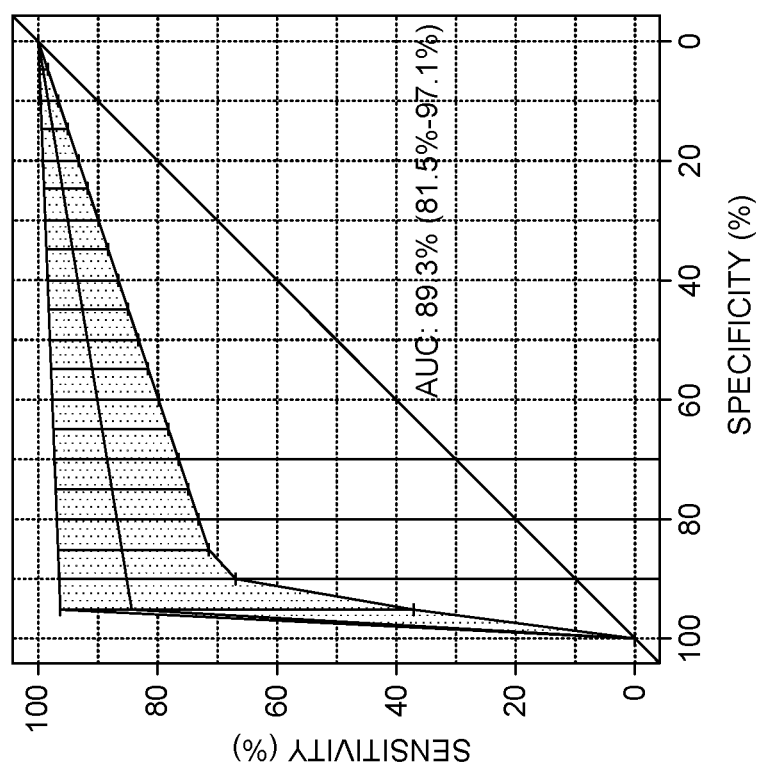

Employing evolutionary algorithms for the identification of the closest (smallest F(x,e)) algebraic skeleton sequences enables those system and method embodiments to achieve relatively high-quality predictions with sequences as short as 4 to 8 elements in length. Further, these embodiments are free of any assumptions regarding any statistical or physiologic dynamical properties of the measurements but instead perform local individual identification of the skeleton algebraic progression for every time step. The Mean Absolute Percentage Error (MAPE)

$$MAPE = \frac{100}{N}\sum_{1}^{N}|x_i - \hat{x}_i|$$

for time series of length 6 is in the range 8% to 27% for the INR series or other series to which the embodiments of the disclosure has been applied (see e.g., FIGS. 3A and 3B). As such, the forecast is sufficiently accurate to serve as an effective advisory aid to physicians wishing to ascertain the approximate risk that the patient will deteriorate (INR<1.8 leading to arterial embolic event) within a time frame comparable to the frequency with which the successive INR measurements are being acquired. Conversely, the forecasts appear also to be sufficiently accurate to serve as an indication that therapeutic maneuvers that have already been undertaken have been effective or adequate (INR≥1.8 and no arterial embolic event) for the recovery of the patient.

With continuing reference to FIG. 2, at a high level, embodiments of methods 200 comprise the following steps. Initially, steps 205 through 215 determine which hemostasis variables to forecast, begin measuring these variables, and censor, clean, or condition the measurements. It is contemplated that some embodiments of method 200, which may determine the variables to be monitored in advance, begin after these initialization and beginning-measurement steps.

At step 205, determine which hemostasis variables to forecast. In one embodiment, method 200 may apply to one variable at time or may be run with a plurality of variables, including in serial or parallel using different variables, which may be determined based on the condition of the patient. Examples of the variables may include variables for determining INR, ISI, or other hemostasis variables, and/or other variables such as described in connection to monitor 141 of FIG. 1A. Additionally, a forecasted variable may be a composite variable of two or more measured variables. Furthermore the rate of measuring the variables may depend on the variable and/or patient condition. In some embodiments, the measured or composite variables that are being used might be displayed to caregiver as part of output of the prediction, using user/clinician interface 142, for example.

At step 210 the variable(s) determined in step 205 are measured and recorded. Embodiments of step 210 may use one or more patient monitors 141, such as a menostasis measurement device to measure and record the variable(s). Measurements may be automated or performed manually, such as by a nurse, and entered. Additionally, an advantage of the time series processing described above, is that some embodiments do not require that the serial measurements be made at precise, periodic intervals but instead tolerate significant clock or phase jitter in the measured time series. At step 215, if necessary, variable value(s) or time points affected by error or measurement artifact are censored. For instance, when a sensor is first attached to a patient, the patient moves, or there is some other disruption, there is a period of stabilization that may be necessary before accurate readings are taken. Step 215 censors out the erroneous readings. Some embodiments of step 215 may also sensor any outlier values measured during the monitoring.

At step 220, newly measured values (or computed composite values, in the case of a composite variable based on several measured variables) are appended to a timeseries of the variable measurements. At step 225, a portion of the time series is determined for using to compute the forecasted variable values. For example, where a patient has been in a hospital for several days, it may only be necessary to use the recent day or hours of data. The size or length of the time series portion determined at step 225 is dependent on the variable(s) being forecasted and/or how often the variable(s) is measured. In some embodiments, "M" of step 225 is six or more. In one embodiment M is between 4 and 50 inclusive. Some embodiment use at least six measurements, but determine a number based on the specific variable being forecasted. Various m lengths are provided in the examples discussed in connection to FIGS. 3A-B and 4A-D.

At step 230, it is determined whether enough measurements have been acquired. If not, then method 200 ultimately goes back to step 210 to continue measuring and recording the variable(s). A minimum number N of measurements needed maybe based on the particular variable being forecasted, for example as described in step 225, some embodiments use at least six measurements (N=six). If there are insufficient measurements, then at step 260, some embodiment of method 200 will wait for a period of time T, such as 12 to 36 hours (and centered on 24 hours, in one embodiment) before going back to step 210. In some embodiments T is a time interval pertinent to the variable(s) being measured. For example, in the case of shock index, T may be at least 12 hours (so step 260 waits for at least 12 hours), in one embodiment. In some embodiments, T may be determined based on the variable being forecasted. For example, if the variable being forecasted exceeds a threshold, then some embodiments may provide a suggested T. (The threshold may be pre-determined and/or may be based on the particular forcasted variable or the patient, and may be adaptive, in some instances.) One practical application of these embodiments means that the decision support system is able to take a greater active role in monitoring the care of the patient.

At step 235, it is determined whether the measurement set determined in step 225 has consistent (identical) values. In some embodiments, where there are unchanging measured variable values (e.g. INR, same heart rate, SpO2 level, etc.) then the evolutionary algorithms used in method 200 have no variability to play with. Accordingly, in some embodiments, method 200 waits (loops back to step 260 and/or step 210) to obtain more readings.

At step 240, the forecasted value(s) are determined. Embodiments of step 240 use the evolutionary algorithms, such as DE and/or PSO described above. In particular, some embodiments further include utilizing an objective function, such as minimizing the Hankel objective function, using the evolutionary algorithms, such as described above. Step 240 may be carried out using the example computer program routines illustratively provided in FIGS. 4A-4D, which use DE and PSO respectively.

Turning briefly to FIGS. 4A-4D, in each of these example embodiments, a Hankel matric is solved with an objective function that is pre-populated with the exponentially weighted average of the existing time series, including those embodiments wherein the time series is as short as 6 measurements long. At the end, we generate the best answer (as contained in the "y5" variable). In some embodiments, the results or estimates may be averaged to reduce noise. For example, in one embodiment, an arithmetic average (which may be implemented as a moving window or boxcar of length 2) may be used for smoothing and noise reduction. Some embodiments of step 240 determine an N number of forecasts. In particular, the determinations using DE and PSO may be performed over many iterations (e.g. tens to hundreds or more iterations) and a central tendency may be determined. In one embodiment, each of the DE and PSO cycles through 50 iterations, generating a forecast each time, which is used to determine a central tendency, which may be combined to form a composite forecast.

Returning to FIG. 2, at step 245 the N forecasts determined in step 240 are combined to create a composite forecast. In one embodiment, the central tendencies determined in step 240 are combined. In one embodiment, the forecasts of two or more evolutionary algorithms are combined using an ensemble method; some embodiments compute an average or weighted average.

In some embodiments, a prediction error is determined for each evolutionary algorithm and used to choose which evolutionary algorithms (or which one algorithm, in the case of two) to use or combine to a composite forecast. In particular, in some cases depending on a physiologic variable and it's values for the patient, one of the DE or PSO (or both) either do not converge or give a forecast value that is so discrepant from the initial exponential weighted moving average value as to be implausible, and is thus rejected. However, typically at least one of DE or PSO will yield a plausible result.

In some embodiments, an additional determination (step 250) may be made as to whether the forecasted value resulting from step 245 (the forecast) is a constant value. That is, the forecast remains constant and does not change from one future time frame (prediction) to the next, for a plurality of future time frames. In some embodiments, which may be based on specific variables, where this situation occurs, method 200 returns back to step 210 (or step 260).

At step 270, it is determined whether the prediction or forecasted value(s) are outside of control limits. In embodiments, control limits are based on the specific variables being used; for example, normal (or reference range) values of INR described herein.

Where the forecast is outside the control limits, then at step 290 an alert may be issued to a caregiver indicating that the patient is forecasted to deteriorate. (It is contemplated that an alert may be issued, or resources scheduled where the patient is forecasted to improve, as well.) Such an alarm may be presented on interface 142, described in connection to FIG. 1A. If the forecast is determined to be within control limits, then pending whether the patient is discharged (step 295) method 200 returns to step 260 and/or step 210 to measure and record additional patient information (if the patient is not discharged) or terminates for this patient at step 280, if the patient is discharged. In some embodiments, if the patient's homeostasis status is forecasted as being in danger of deteriorating, the alert may contain instructions for the sensor (or system implementing method 200) to reduce the time (T) between measurements.

With reference now to FIGS. 3A-3C, the results of example embodiments actually reduced to practice are illustratively provided. These embodiments include performing evolutionary analysis to generate a statistical forecast for the next epoch immediately beyond the present one, based on data from as few as four serial measurement epochs, wherein the epoch is based in part on the specific measured variable(s).

With reference to FIG. 5, column 502 represents a particular case or particular patient. Column 504 contains the temporal sequence that corresponds to the time of measurements of a particular patient. Column 506 represents the age category of the particular patient. Column 508 represents the particular patient's gender, while column 510 contains homeostasis measurements that were measured through medical instrumentation.

For these embodiments actually reduced to practice, a server cluster running the Linux operating system (as Operating System 129 of FIG. 1A) was used along with the computer program routines illustratively presented in FIGS. 4A-4D, using the open-source statistical software package R, and the R modules DEoptim and pso (as services 124 and 126 of FIG. 1A). A set of de-identified, secondary-use-consented, EHR-derived, HIPAA-compliant vital signs measurements from 100 human patients whose care episodes had previously been completed and for whom the outcomes were already known was extracted from a commercially-available datawarehouse (Cerner Health Facts®). For some of these embodiments, INR time-series were computed for each of the 100 subjects and next-value forecasts were generated using PSO. The MAPE for 7-day monitoring timeseries was calculated for each and the statistical sensitivity, specificity, and ROC area-under the curve (AUC) was computed, as shown in FIGS. 3A and 3B. These figures demonstrate that the practical application of the embodiments generate profound advantages over prior conventional technological solutions.

In particular, FIGS. 3A and 3B depicts the receiver operating characteristic (ROC) curve of the forecasting system and method set forth in embodiments of the disclosure, as applied to the computation of forecasts for the shock index. FIG. 3C depicts an example computer program routine for determining the ROC illustrated in FIG. 3A. As is known to those practiced in the art, the area under the ROC curve is a standard means of quantitatively assessing a classifier model's discrimination, the degree to which the model is able to accurately categorize cases into one or the other of two classes or categories—in this instance, "will acutely deteriorate to a hypercoagulable, arterial embolism-prone state" (sub-therapeutic INR<1.8) vs. "will not acutely deteriorate" (INR≥1.8). Embodiments thus provide healthcare professionals an enhanced ability to monitor and anticipate the patient's future status, which results in altering the care the patient would have otherwise received.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Not all steps listed in the various figures need be carried out in the specific order described. Accordingly, the scope of the disclosure is intended to be limited only by the following claims.

What is claimed is:

1. Computer-readable media having computer-executable instructions embodied thereon that when executed by at least one computer processor, facilitate a method for periodically monitoring at least one patient, the method comprising:
   collecting hemostasis data for the at least one patient, wherein the hemostasis data comprises a set of data points collected at a plurality of data measurement times by one or more hemostasis sensors, and wherein each data point of the set of data points includes a corresponding date-time stamp;
   generating a time series comprising a plurality of the set of data points and the corresponding date-time stamps;
   generating a patient forecast using particle swarm optimization, the patient forecast comprising predicted hemostasis parameters for the at least one patient at a future time based on the time series;
   determining that the patient forecast is within a control limit range associated with the collected hemostasis data; and
   based on the predicted hemostasis parameters, generating instructions to modify a treatment program associated with the at least one patient to prevent a future occurrence of the patient forecast.

2. The media of claim 1, wherein the particle swarm optimization comprises algorithms that perform population-based stochastic searches and that remove noise.

3. The media of claim 1, wherein the hemostasis data is collected from an electronic health record (EHR) computer system.

4. The media of claim 1, further comprising:
   computing a shock index using the hemostasis data;
   storing the shock index as a plurality of serial determinations over time; and
   generating the time series using the plurality of serial determinations over time.

5. The media of claim 1, wherein the particle swarm optimization is used to solve a value of a physiologic variable or a composite variable at a plurality of future time points.

6. The media of claim 5, further comprising combining values of the physiologic variable or the composite variable for generating the patient forecast.

7. The media of claim 6, wherein the combining comprises an arithmetic mean or a median of the values of the physiologic variable or the composite variable.

8. The media of claim 6, wherein the combining comprises an exponentially weighted moving average or other linear combination of the values.

9. The media of claim 6, wherein the combining comprises a minimum or a maximum of the values.

10. The media of claim 6, wherein the combining comprises applying a digital filter to the values.

11. The media of claim 1, wherein the time series comprise serial measurements that are represented as a Hankel matrix.

12. The media of claim 5, wherein the time series comprise serial measurements that are represented as a Hankel matrix, and wherein the particle swarm optimization uses an objective function that minimizes a determinant of the Hankel matrix, either alone or with one or more additional terms of the objective function.

13. A computer-implemented method for assessing a patient comprising:
   receiving hemostasis data of the patient, wherein the hemostasis data comprises a set of data points collected at a plurality of data measurement times by one or more hemostasis sensors, and wherein each data point of the set of data points includes a date-time stamp;
   generating a time series, the time series comprising at least six data points of the set of data points and based on the date-time stamp;
   generating a patient forecast using particle swarm optimization, the patient forecast comprising predicted hemostasis parameters for the patient at a future time based on the time series; and
   based on the predicted hemostasis parameters, generating instructions to modify a treatment program associated with the patient to prevent a future occurrence of the patient forecast.

14. The computer-implemented method of claim 13, wherein the hemostasis data is represented in a Hankel matrix, and wherein the particle swarm optimization uses an objective function that minimizes a determinant of the Hankel matrix, either alone or with one or more additional terms of the objective function.

15. The computer-implemented method of claim 13, wherein the method further comprises providing an alert for the patient to contact a health-care provider based on the predicted hemostasis parameters.

16. A patient monitoring system for periodically monitoring at least one patient using a particle swarm optimization to prevent a future occurrence of a hemodynamic deterioration, the system comprising:
   one or more sensors configured to collect hemostasis data for the at least one patient;
   a processor; and
   computer storage memory having computer-executable instructions stored thereon which, when executed by the processor, implement a method of monitoring the at least one patient, the method comprising:
      collecting hemostasis data of the at least one patient, wherein the hemostasis data comprises a set of data points collected at a plurality of data measurement times from the one or more sensors, and wherein each data point of the set of data points includes a date-time stamp;
      generating a time series, the time series comprising at least six data points of the set of data points and based on the date-time stamp;
      calculating, using particle swarm optimization, predicted hemostasis parameters for the at least one patient at a future particular time based on the time series comprising the at least six data points of the set of data points; and
      based on the predicted hemostasis parameters, generating instructions to modify a treatment program associated with the at least one patient to prevent a future occurrence of hemodynamic deterioration.

17. The system of claim 16, wherein the hemostasis data is formatted as a Hankel matrix, and wherein the particle swarm optimization uses an objective function that minimizes a determinant of the Hankel matrix, either alone or with one or more additional terms of the objective function.

18. The system of claim 16, further comprising instructing the one or more sensors to reduce the time between the plurality of data measurement times between the data points in the set of data points.

19. The system of claim 16, wherein the collected hemostasis data comprises an INR time series.

20. The system of claim 16, wherein the hemodynamic deterioration is an acute deterioration.

* * * * *

UNITED STATES PATENT AND TRADEMARK OFFICE
CERTIFICATE OF CORRECTION

PATENT NO. : 10,910,110 B1
APPLICATION NO. : 15/292938
DATED : February 2, 2021
INVENTOR(S) : Douglas S. McNair It is certified that error appears in the above-identified patent and that said Letters Patent is hereby corrected as shown below:

In the Specification

Column 09, Line 47: Please remove "solution" and replace with --soliton--.

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*